United States Patent [19]

Wildsmith

[11] 3,980,785

[45] Sept. 14, 1976

[54] SECONDARY AND TERTIARY-2-PHENYLBICYCLO[2,2,2]OCT-3-YL ALKYLAMINES AND COMPOSITION THEREOF

[75] Inventor: Eric Wildsmith, Lancaster, England

[73] Assignee: Lilly Industries, Ltd., London, England

[22] Filed: Aug. 11, 1975

[21] Appl. No.: 603,230

Related U.S. Application Data

[63] Continuation-in-part of Ser. No. 411,881, Nov. 1, 1973.

[30] Foreign Application Priority Data

Nov. 4, 1972 United Kingdom............ 505931/72

[52] U.S. Cl................................. 424/266; 260/141; 260/295.5 S; 260/349; 260/453 AR; 260/465 E; 260/465 F; 260/465 G; 260/471 A; 260/473 R; 260/501.1; 260/501.21; 260/515 R; 260/515 A; 260/518 R; 260/521 R; 260/544 N; 260/558 R; 260/558 A; 260/567.5; 260/570.5 CA; 260/571; 260/576; 260/578; 260/599; 260/618 H; 424/316; 424/330

[51] Int. Cl.²...................................... A61K 31/455

[58] Field of Search.................. 260/295.5 S, 501.1, 260/501.21, 570.5 CA; 424/266, 316, 330

[56] References Cited

UNITED STATES PATENTS 3,742,055  6/1973  Freedman....................... 260/570.5

*Primary Examiner*—Robert V. Hines
*Attorney, Agent, or Firm*—William B. Scanlon; Everet F. Smith

[57] ABSTRACT

Secondary and tertiary 2-phenylbicyclo[2,2,2]oct-3-yl alkyl amines are useful as anti-depressant and anti-Parkinsonism agents. They may be prepared from the corresponding aldehydes, nitriles, amides, isocyanates or esters using known chemical techniques.

16 Claims, No Drawings

SECONDARY AND TERTIARY-2-PHENYLBICYCLO[2,2,2]OCT-3-YL ALKYLAMINES AND COMPOSITION THEREOF

CROSS-REFERENCE

This application is a continuation-in-part of my copending application Ser. No. 411,881, filed Nov. 1, 1973.

This invention relates to a new class of drugs having useful central nervous system activity. These drugs are characterised by having a 2-phenylbicyclo[2,2,2]octane nucleus, which is a nucleus not hitherto found in drugs of this type. The invention provides methods by which said novel drugs may be prepared, as well as pharmaceutical compositions comprising said drugs.

The novel 2-phenylbicyclo octane compounds of the present invention have the formula:

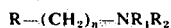   I.

and acid addition salts thereof, wherein $n$ is an integer from 1 to 3, $R_1$ is $C_{1-4}$ alkyl, $R_2$ is hydrogen or $C_{1-4}$ alkyl and R is a trans 2-phenylbicyclo[2,2,2]oct-3-yl group of formula:

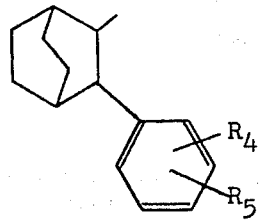   (II)

wherein $R_4$ and $R_5$ represent the same or a different substituent selected from hydrogen, halogen, nitro, amino, mono- or di-$C_{1-4}$ alkylamino, $C_{1-4}$ alkyl or $C_{1-4}$ alkoxy.

Preferred compounds of formula (I) are those having one or more of the following features:

a. $n$ is 1 or 2;
b. $R_5$ is hydrogen and $R_4$ is halogen, nitro, amino, methyl- or ethyl amino, dimethyl- or diethyl-amino, methyl, ethyl, methoxy or ethoxy in the 4-position;
c. $R_4$ and $R_5$ are both hydrogen;
d. $R_4$ and $R_5$ are both halogen in the 3,4-position;
e. $R_1$ is $C_{1-4}$ alkyl and $R_2$ is hydrogen, methyl or ethyl;
f. $n$ is 1, $R_1$ and $R_2$ are both methyl, $R_4$ is a m-halo substituent and $R_5$ is hydrogen.

Most advantageously, the compounds of formula (I) have the features (a), (b) and (e), (a), (c) and (e), or (a), (d) and (e), or the feature (f), listed above.

For the avoidance of doubt, the term "$C_{1-4}$ alkyl" as used herein, whether explicitly or implicitly, is intended to encompass any straight or branched chain alkyl group having from 1 to 4 carbon atoms. Thus $R_1$ and/or $R_2$ may be a methyl, ethyl, n-propyl, isopropyl, n-butyl, isobutyl, s-butyl, or t-butyl group.

The compounds of formula (I) may be prepared by any of the normal methods for preparing substituted alkyl amines. The preferred methods of preparation according to the present invention involve the use of an intermediate of formula:

   III.

where R is as defined above, $m$ is 0, 1 or 2 and $R_3$ represents —CHO, —CN, —CONR$_6$R$_7$ where $R_6$ and $R_7$ are independently hydrogen or $C_{1-4}$ alkyl, —CH$_2$NCO or —COOR$_8$ where $R_8$ is $C_{1-4}$ alkyl, which may, if convenient, be reacted in situ in the reaction medium in which it is formed.

The compounds of formula (III) are readily converted to compounds of formula (I) by reduction. In the case of the nitriles and amides of formula (III), the reduction is preferably carried out using a complex hydride reducing agent such as lithium aluminium hydride or sodium borohydride, whilst in the case of the isocyanates of formula (III), treatment with a concentrated mineral acid such as hydrochloric acid produces the desired conversion. The aldehydes and esters of formula (III) may be reductively aminated to the desired compounds of formula (I) by reduction to the corresponding alcohols, for example, using a complex hydride reducing agent, conversion of the alcohols to the corresponding alkyl or aryl sulphonates (by reaction with an alkyl or aryl sulphonyl chloride such as methyl sulphonyl chloride or p-toluene sulphonyl chloride) and reaction of the sulphonates with an amine of formula HNR$_6$R$_7$. Reductive amination of the aldehydes of formula III may also be carried out by catalytic hydrogenation in the presence of an amine of formula HNR$_6$R$_7$.

Where $R_3$ is —CN, —CONH$_2$ or CH$_2$NCO, or the above-mentioned reductive amination is carried out in the presence of ammonia, the resultant product of formula I is a primary amine which is then alkylated to produce a compound of formula I in which $R_1$ and/or $R_2$ is $C_{1-4}$ alkyl. The alkylation may be carried out in conventional manner, for example by reductive alkylation, reaction with an alkyl halide or sulphate, reaction with an alkyl chloroformate followed by reduction of the resultant urethan or, when methylation is to be carried out, preferably by reaction with formic acid/formaldehyde.

The compounds of formula I produced by the foregoing process may be isolated per se or in acid addition salt form.

The acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, malic, tartaric, citric, salicylic, o-acetoxybenzoic, nicotinic or isonicotinic acid, or organic sulphonic acids for example methane sulphonic, ethane sulphonic, 2-hydroxyethane sulphonic, toluene-p-sulphonic, or naphthalene-2-sulphonic acid. Apart from pharmaceutically acceptable acid addition salts, other salts are also included within the scope of acid addition salts such as, for example, those with picric or oxalic acid; they may serve as intermediates in the purification of the compounds or in the preparation of other, for example, pharmaceutically acceptable, acid addition salts, or are useful for identification, characterization or purification of the bases.

A resulting acid addition salt may be converted into the free compound according to known methods, for example, by treating it with a base, such as with a metal hydroxide or alkoxide, for example an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium potassium or calcium carbonate or hydrogen carbonate; with ammonia; or with a hydroxyl ion exchange preparation, or with any other suitable reagent.

A resulting acid addition salt may also be converted into another acid addition salt according to known methods; for example, a salt with an inorganic acid may be treated with a metal salt, for example a sodium, barium or silver salt, of an acid in a suitable diluent, in which a resulting inorganic salt is insoluble and is thus removed from the reaction medium. An acid addition salt may also be converted into another acid addition salt by treatment with an anion exchange preparation.

The above intermediates of formula III, with the exception of the compound in which $m$ is 0, $R_3$ is —CN, $R_4$ is p-chloro and $R_5$ is hydrogen, are new compounds and accordingly they also form a part of this invention.

They may be obtained from a trans-6-phenylbicyclo[2,2,2]oct-2-ene-5-carboxaldehyde (which is prepared by a Diels-Alder reaction between the appropriate trans cinnamaldehyde and 1,3-cyclohexadiene)

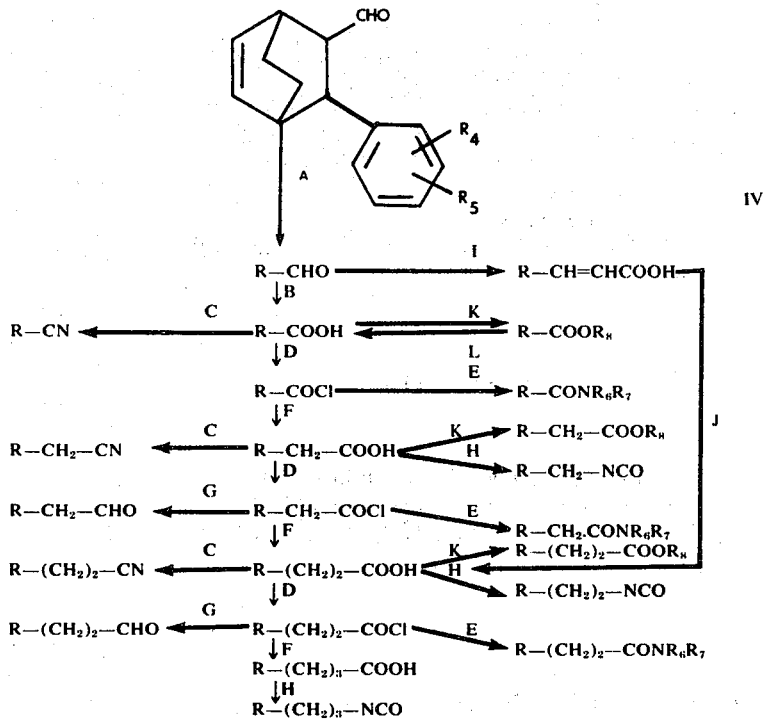

according to the following reaction sequences in which $R$, $R_1$, $R_2$, $R_4$, $R_5$, $R_6$, $R_7$ and $R_8$ are as defined above.

Reaction A above involves the reduction of the compound of formula IV using, for example, hydrogen in the presence of a suitable catalyst such as palladium on charcoal, to produce the aldehyde of formula III in which $m$ is 0. Reaction B is accomplished by oxidation as is well known in the art and the resultant carboxylic acid may then be converted to the corresponding acid chloride-reaction D - in conventional manner, for example by reaction with thionyl chloride. The latter may then be converted by the Arndt-Eistert synthesis - reaction F - to a substituted acetic acid and, by repetition of reactions D and F, the correspondingly substituted propionic and butyric acid may be obtained. The aforementioned substituted propionic acid may also be prepared from the aldehyde R-CHO by reactions I and J, reaction I being the well-known Knoevenagel reaction to produce a 3-substituted acrylic acid and reaction J involving the reduction of the acrylic acid using, for example, hydrogen over a palladium catalyst to produce the desired propionic acid.

By reaction C, the aforementioned carboxylic acid, substituted acetic acid or substituted propionic acid may be converted to the corresponding nitriles of formula III in which $m$ is 0, 1 or 2. Reaction C may be carried out by treatment of the acid with ammonia at elevated temperatures in the presence of alumina.

The nitriles of formula III in which $m$ is 0 can also be made directly by the following reaction sequence:

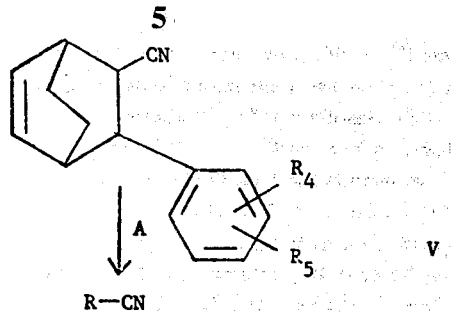

where reaction A is as described above, the compound of formula V being obtained by a Diels-Alder reaction between the appropriate trans β-cyanostyrene and 1,3-cyclohexadiene.

The acid chlorides produced by reaction D above are readily converted — reaction E — to the desired amides of formula III by reaction with the appropriate amine of formula $HNR_6R_7$. Additionally by reduction of substituted acetyl and propionyl chlorides produced above — reaction G — the required aldehydes of formula III in which m is 1 or 2 may be obtained. The well known Rosenmund reaction provides one means of accomplishing this reduction.

The above mentioned substituted acetic, propionic and butyric acids may also be converted — reaction H — to the desired isocyanates of formula III in which m is 0, 1 or 2. This conversion may be accomplished by forming the corresponding acid azide either by treatment of the corresponding acid chloride with sodium azide or by formation of the corresponding acid hydrazide and treatment of the latter with nitrous acid, and then heating the acid azide in benzene or chloroform solution.

Reaction K involves the conventional esterification of the corresponding acid, for example by reaction with an alcohol $R_8$—OH. The esters of formula III in which m is 0 can also be prepared by the following reaction sequence:

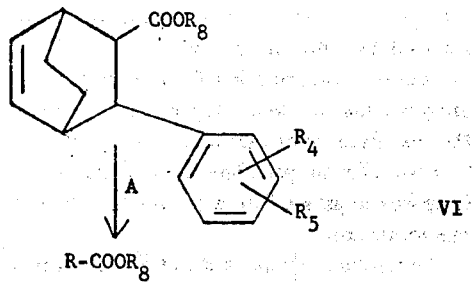

wherein reaction A is as described above, the compound of formula VI being obtained by a Diels-Alder reaction between the appropriate alkyl ester of a trans cinnamic acid and 1,3-cyclohexadiene. The resultant ester may then be hydrolysed — reaction L — to yield the corresponding acid.

As stated above, reaction A involves reduction, for example by means of catalytic hydrogenation, and it will therefore be appreciated by those skilled in the art that, if $R_4$ or $R_5$ is a nitro group, the latter may be partially or entirely reduced to the corresponding amino substituted product. Accordingly, if a nitro substituted end product is desired, the appropriate intermediate of formula III is preferably obtained by nitration after reaction A has been carried out and the subsequent conversion of the nitrated intermediate to the desired compound of formula I carried out under conditions which will not reduce the nitro substituent. For example the reductive amination of a nitrated aldehyde of formula III may be carried out using sodium borohydride, followed by conversion of the resultant alcohol to an alkyl or aryl sulphonate derivative and reaction of the latter with an amine of formula $HNR_6R_7$.

It will also be appreciated by those skilled in the art that a resultant compound of formula I in which $R_4$ or $R_5$ is an amino group can be converted to other compounds of formula I in conventional manner. Thus, the amino substituted compound may be acylated to produce a desired product of formula I in which $R_4$ or $R_5$ is a $C_{2-5}$ acylamino group or mono- or di-alkylated to produce a desired compound in which $R_4$ or $R_5$ is a mono- or di-$C_{1-4}$ alkylamino group. Further the amino substituted product may be diazotized and the resultant diazonium salt converted to a variety of other products, for example by decomposition in an alcohol to yield the corresponding $C_{1-4}$ alkoxy substituted compound or by reaction with a cuprous halide to yield the corresponding halo substituted compound of formula I.

The compounds of the present invention possess anti-depressant, anti-psychotic and anti-Parkinsonism activity and hence are useful for the treatment of various depressive states in mammals as well as providing relief of Parkinsonism. The usefulness of the compounds of formula I has been demonstrated in well known test procedures such as antagonism of reserpine hypothermia in mice and reserpine catalepsy in rats. Certain of the compounds of formula I also display anorectic and/or analgesic activity.

As noted above, the compounds of the present invention form acid addition salts and, where such salts are pharmaceutically acceptable, they are equally useful for the treatments mentioned previously. The compounds and the pharmaceutically acceptable acid addition salts thereof of this invention are effective over a wide dosage range, the actual dose administered being dependent on such factors as the particular compound being used, the condition being treated and the type and size of mammal being treated. However, the dosage required will normally fall within the range of 0.1 to 100 mg./Kg. per day, for example in the treatment of adult humans dosages of from 0.5 to 15 mg./Kg. may be used whilst, in the treatment of test animals such as mice and rats, dosages of from 5 to 75 mg./Kg. may be employed.

The compounds and salts of the present invention will normally be administered orally or by injection and, for this purpose, said compounds and salts will usually be utilised in the form of a pharmaceutical composition. Such compositions are prepared in a manner well known in the pharmaceutical art and normally comprise at least one active compound or salt of the invention in association with a pharmaceutically acceptable carrier therefor. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate or mineral oil. The compositions of the invention may, as is well known in the art, be formulated so as to provide quick, sustained or delayed release of the active ingredient after administration to the patient.

Depending on the route of administration, the foregoing compositons may be formulated as tablets, capsules or suspensions for oral use and injection solutions for parenteral use. Preferably the compositions are formulated in a dosage unit form, each dosage containing from 1 to 500 mg., more usually 5 to 250 mg., of the active ingredient.

The following Examples illustrate test procedures used to demonstrate the activity of the compounds of the invention:

EXAMPLE A — ANTAGONISM OF RESERPINE HYPOTHERMIA IN MICE:

Groups of 5 mice weighing 19 – 25 g. were placed individually in cages (6 inch × 4 inch) and injected with 4 mg./Kg. reserpine subcutaneously in a dose volume of 0.2 ml.

Two and a half hours after the reserpine injection, the test compounds were administered subcutaneously to groups of mice at doses approximately ¼ and ⅛ of the previously calculated $LD_{50}$ i.p. Rectal temperatures were recorded immediately before the drugs were injected. Further temperature recordings were taken at 30 minute intervals up to 1½ hours after drug administration, the temperature being recorded with a thermocouple. On each experiment a group of control mice were used, these being dosed with saline in place of the test compound.

In order to simplify the recording of results, the "temperature index" assessment described by Winter and Nuss, Toxicology and Applied Pharmacology, 5, 247 – 56, (1963), was used. Taking as a base the mean initial temperature for each group, the mean temperature changes from this figure at 30, 60 and 90 minutes were summed and termed the "temperature index (T.I.)". Using this system, mice given reserpine alone gave temperature indices in the range of −5 to −15. If the T.I. of the control group was less than −5 or greater than −15, the experiment was repeated.

The results of the evaluation are reported in the Table below, with "±" symbolising a T.I. of from 2.5 to 5 units hyperthermic from the control group, with "+" symbolising a T.I. of from 5 to 10 units hyperthermic from the control group, "++" symbolising a T.I. of 11 to 15 units hyperthermic from the control group, and "+++" symbolising a T.I. of 16–20 units hyperthermic.

EXAMPLE B — ANTAGONISM OF RESERPINE CATALEPSY IN RATS.

Groups of 4 rats (female Wistar) weighing 160 – 200 g. were injected with 5 mg./Kg. reserpine subcutaneously in a dose volume of 1 ml. Seventeen hours later the rats were tested to see if they were cataleptic using the following four tests adapted from the method of Simon, Langwinski and Boissier, Therapie, 24, 985 – 995;

(a) A hind leg was placed on a 3 cm. high cork.
(b) A hind leg was placed on a 9 cm. high cork.
(c) The rat was straddled across parallel bars approximately 10 cm. apart.
(d) The rat was placed on a vertical grid.

A rat was given a score of 2 for each test if it did not move from the position it was placed in for 20 seconds, and a score of 1 was given for any rat making only a slight movement. Any rat scoring less than six out of eight was rejected.

Immediately after testing for catalepsy, the rats were dosed orally with a test compound at a dose of 40 or 20 mg./Kg. in a dose volume of 1 ml. The degree of catalepsy was again assessed ½, 1, 1½, 2½, 3½ and 4½ hours after the drugs were administered.

On each experiment, a group of control rats were dosed only with saline.

Using a computer programme based on the Chi-squared test, the degree of reversal of catalepsy was calculated by comparing the area of the graph of catalepsy versus the time elapsed since administration of the test drug, with the maximum possible area, i.e. no reversal of catalepsy. The area of the graph of the test drug was expressed as a percentage reduction of the maximum area.

The results are reported in the following Table, with "+" symbolizing a percentage reduction in maximum area of 10 – 25% (provided p <0.05), with "++" symbolizing a percentage reduction in maximum area of 25 – 50%, and "+++" symbolizing greater than 50%.

TABLE

| Test Compound (R being as defined in Formula I and $R_1$ and $R_5$ being as shown) in hydrochloride salt form | Example A Reserpine hypothermia in mice Dose (s.c.) in mg./Kg. | Result | Example B Reserpine catalepsy in rats Dose (p.o.) in mg./Kg. | Result |
|---|---|---|---|---|
| R = $CH_2$—$NHCH_3$ | 20 | ± | 40 | 0 |
| $R_1$ = $R_5$ = H | 10 | ± | 20 | 0 |
| R = $CH_2$—$N(CH_3)_2$ | 20 | + | 40 | +++ |
| $R_1$ = $R_5$ = H | 10 | + | 20 | + |

TABLE -continued

| Test Compound (R being as defined in Formula I and $R_4$ and $R_5$ being as shown) in hydrochloride salt form | Example A Reserpine hypothermia in mice Dose (s.c.) in mg./Kg. | Result | Example B Reserpine catalepsy in rats Dose (p.o.) in mg./Kg. | Result |
|---|---|---|---|---|
| $R—(CH_2)_2—NHCH_3$ | 20 | ± | 40 | +++ |
| $R_4 = R_5 = H$ | 10 | + | 20 | + |
| $R—(CH_2)_2—N(CH_3)_2$ | 25 | + | 40 | ++ |
| $R_4 = R_5 = H$ | 12.5 | 0 | 20 | + |
| $R—(CH_2)_3—NHCH_3$ | 20 | ± | 40 | 0 |
| $R_4 = R_5 = H$ | 10 | + | 20 | 0 |
| $R—CH_2—NHC_2H_5$ | 40 | + | 40 | +++ |
| $R_4 = R_5 = H$ | 20 | + | 20 | ++ |
| $R—CH_2—N\begin{smallmatrix}CH_3\\C_2H_5\end{smallmatrix}$ | 40 | ++ | 40 | +++ |
| $R_4 = R_5 = H$ | 20 | + | 20 | ++ |
| $R—CH_2—N(C_2H_5)_2$ | 40 | + | 40 | ++ |
| $R_4 = R_5 = H$ | 20 | ± | 20 | ++ |
| $R—CH_2—N\begin{smallmatrix}CH_3\\(CH_2)_2CH_3\end{smallmatrix}$ | 25 | + | / | + |
| $R_4 = R_5 = H$ | 12.5 | 0 | 20 | 0 |
| $R—CH_2—N(CH_3)_2$ | 20 | + | 40 | ++ |
| $R_4 = p\text{-Cl}, R_5 = H$ | 10 | ++ | 20 | + |
| $R—CH_2—N\begin{smallmatrix}CH_3\\C_2H_5\end{smallmatrix}$ | 25 | ++ | 40 | + |
| $R_4 = p\text{-Cl}, R_5 = H$ | 12.5 | 0 | 20 | + |
| $R—CH_2—N(CH_3)_2$ | 25 | 0 | NT* | |
| $R_4 = p\text{-N(CH}_3)_2, R_5 = H$ dihydrochloride | 12.5 | + | | |
| $R—CH_2—N(CH_3)_2$ | 25 | + | NT* | |
| $R_4 = p\text{-NH}_2, R_5 = H$ dimaleate | 12.5 | + | | |
| $R—CH_2—N(CH_3)_2$ | 50 | + | NT* | |
| $R_4 = p\text{-NHCOCH}_3, R_5 = H$ | 25 | 0 | | |
| $R—CH_2—N(CH_3)_2$ | 12.5 | +++ | 5 | +++ |
| $R_4 = m\text{-Cl}, R_5 = H$ | | | | |

*= Not tested.

The following Examples will illustrate the preparation of the novel intermediates of formula III above:

EXAMPLE 1 trans-6-Phenylbicyclo[2,2,2]oct-2-ene-5-carboxaldehyde (70.7 g.) was hydrogenated in ethyl acetate (250 ml.) over 5% palladium on charcoal (2 g.) at a pressure of 60 pounds/sq. in. for 1 hour at room temperature. The catalyst was removed by filtration and the product isolated by distillation by yield trans-2-phenylbicyclo[2,2,2]octane-3-carboxaldehyde (63 g.), b.p. 112° – 114°C./0.2 mm.

Similarly the following aldehydes were prepared:
trans-2-p-methylphenylbicyclo[2,2,2]octane-3-carboxaldehyde
trans-2-p-chlorophenylbicyclo[2,2,2]octane-3-carboxaldehyde
trans-2-(2',4'-dimethylphenyl)bicyclo[2,2,2]octane-3-carboxaldehyde
trans-2-p-aminophenylbicyclo[2,2,2]octane-3-carboxaldehyde
trans-2-p-bromophenylbicyclo[2,2,2]octane-3-carboxaldehyde

EXAMPLE 2 a. The 2-phenyl aldehyde from Example 1 (5.75 g.) was dissolved in pyridine (15 ml.) and piperidine (300 mg.), and malonic acid (9.0 g.) added. The mixture was heated gently on a steam bath for 1.25 hours after which time $CO_2$ evolution had become quite slow. The solution was heated under reflux for 1 hour, then poured into excess 3N hydrochloric acid containing crushed ice and the mixture extracted three times into dichloromethane. The extracts were dried ($MgSO_4$), evaporated and the resultant crystals were re-crystallised from ethanol to give 3-(trans-2-phenylbicyclo[2,2,2]oct-3-yl) acrylic acid (6.0 g.), m.p. 138° – 139°C.

b. The acrylic acid from (a) above (14.6 g.) was dissolved in ethanol (200 ml.) and hydrogenated over 5% palladium on charcoal (1 g.) at 60 pounds/sq. in. at room temperature for 1.5 hours. The solution was filtered and evaporated to give a white solid which was re-crystallised from dichloromethane/petroleum ether to give 3-(trans-2-phenylbicyclo[2,2,2]oct-3-yl)propionic acid (13.1 g.), m.p. 112° – 114°C.

c. The acid from (b) above (20.64 g.) was dissolved in acetone (100 ml.) and the solution cooled to 0°C. Triethylamine (10.1 g.) was added followed by ethyl chloroformate (9.5 g.) giving a white precipitate and the suspension was stirred for 45 minutes at 0°C. Ammonia (9.0 g.; S.G. 0.88) was then added and the solution stirred overnight allowing warming to room temperature. The resultant solution was heated on a steam bath and water added until crystallisation occurred. On re-crystallisation from ethanol/water, there was obtained 3-(trans-2-phenylbicyclo[2,2,2]oct-3-yl)propionamide, m.p. 122° – 123°C.

EXAMPLE 3

3-(trans-2-Phenylbicyclo[2,2,2]oct-3-yl)propionic acid (25.8 g.) was dissolved in acetone (500 ml.) and triethylamine (12.1 g.) added. Water (100 ml.) was added and the solution cooled to 0°C. Ethyl chloroformate (11.93 g.) was added dropwise to the cooled solution and stirring was continued for 30 minutes at 0°C. A solution of sodium azide (9.7 g.) in water (50 ml.) was added causing immediate precipitation of sodium chloride. The solution was allowed to warm to room temperature and after 1 hour the bulk of the acetone was removed under reduced pressure. Water (about 500 ml.) was added and the solution extracted three times with methylene chloride. The combined extracts were dried over magnesium sulphate, filtered and evaporated to give an oil. Any residual water was removed by taking up the oil in toluene and evaporating the solution under reduced pressure. The infra-red spectrum of the oil showed an azide band at 2140 cm.$^{-1}$. The yield of azide was 28.3 g. The latter was dissolved in dry benzene and the temperature raised slowly to the boiling point of the mixture. Nitrogen was evolved steadily for around 10 minutes after which heating was continued for a further 15 minutes at which point infra-red spectroscopy revealed no residual azide. Evaporation of the benzene solution gave 2-(trans-2-phenylbicyclo[2,2,2]oct-3-yl)ethyl isocyanate as an oil (25 g.). Similarly the following isocyanates were prepared from the corresponding acids:

trans-2-p-chlorophenylbicyclo[2,2,2]oct-3-yl methyl isocyanate trans-2-phenylbicyclo[2,2,2]oct-3-yl methyl isocyanate trans-2-p-nitrophenylbicyclo[2,2,2]oct-3-yl methyl isocyanate trans-2-p-methylphenylbicyclo[2,2,2]oct-3-yl methyl isocyanate trans-2-p-N,N-diethylaminophenylbicyclo[2,2,2]oct-3-yl methyl isocyanate trans-2-p-methoxyphenylbicyclo[2,2,2]oct-3-yl methyl isocyanate trans-2-p-aminophenylbicyclo[2,2,2]oct-3-yl methyl isocyanate trans-2-p-3′,4′-dimethylphenylbicyclo[2,2,2]oct-3-yl methyl isocyanate trans-2-p-3′,4′-dichlorophenylbicyclo[2,2,2]oct-3-yl methyl isocyanate 2-(trans-2-p-chlorophenylbicyclo[2,2,2]oct-3-yl)ethyl isocyanate 2-(trans-2-p-aminophenylbicyclo[2,2,2]oct-3-yl)ethyl isocyanate 3-(trans-2-p-aminophenylbicyclo[2,2,2]oct-3-yl)propyl isocyanate 3-(trans-2-p-N-acetylaminophenylbicyclo[2,2,2]oct-3-yl)propyl isocyanate

EXAMPLE 4 trans-2-Phenylbicyclo[2,2,2]octane-3-carboxaldehyde (10 g.) was oxidised using Jones' Reagent (chromium trioxide/sulphuric acid) to produce the corresponding 3-carboxylic acid which, on treatment as described in Example 2 (c), yielded trans-2-phenylbicyclo[2,2,2]octane-3-carboxyamide, m.p. 121° – 122°C. after two re-crystallisations from ethanol/water.

In similar fashion, but carrying out the step of Example 2 (c) using dimethylamine in place of ammonia, N,N-dimethyl trans-2-phenylbicyclo[2,2,2]-octane-3-carboxyamide was obtained.

EXAMPLE 5 trans-2-Phenylbicyclo[2,2,2]octane-3-carboxaldehyde (0.1 mole) was oxidised as described in Example 4 to produce the corresponding 3-carboxylic acid which was converted to the acid chloride by treatment with thionyl chloride. Reaction of the acid chloride with diazomethane (0.2 moles) followed by addition of water and warming in the presence of silver oxide produced the expected 2-(trans-2-phenylbicyclo[2,2,2]oct-3-yl acetic acid. The latter can be converted to the corresponding amide by the method of Example 2 (c), to the corresponding isocyanate by the method of Example 3, to the corresponding ester by reaction with a $C_{1-4}$ alcohol, to the corresponding trans-2-phenylbicyclo[2,2,2]oct-3-yl acetonitrile by heating with ammonia in the presence of alumina, or to the corresponding trans-2-phenylbicyclo[2,2,2]oct-3-yl acetaldehyde by forming the corresponding acetyl chloride and submitting the latter to a Rosenmund reduction. Similarly 2-substituted phenyl compounds of formula III are prepared.

EXAMPLE 6 trans-p-Methylcinnamic acid, ethyl ester (4 g.), cyclohexadiene (10 ml.) and benzene (5 ml.) were heated for 3 weeks at 155°C. The mixture was then distilled to yield ethyl trans-6-p-methylphenylbicyclo[2,2,2]oct-2-ene-5-carboxylate which, on reduction as described in Example 1, gave ethyl trans-2-p-methylphenylbicyclo[2,2,2]octane-3-carboxylate as an oil. In the same manner, the corresponding 2-p-chlorophenyl, 2-p-methoxyphenyl, 2-p-N,N-dimethylaminophenyl, 2-p-aminophenyl compounds and 2-phenyl compounds were prepared. Nitration of the latter gave the corresponding 2-p-nitrophenyl compound.

EXAMPLE 7 trans-3,4-Dichlorocinnamonitrile (20 g.) and cyclohexadiene (16 g.) were heated at 150°C. for 3 weeks. The solution was evaporated, the resultant oil purified by column chromatography and crystallised from methanol to yield white crystals of 5-cyano-6-(3′,4′-dichlorophenyl)bicyclo[2,2,2]oct-2-ene. The latter (14 g.) was hydrogenated as described in Example 1 to yield trans-3-cyano-2-(3′,4′-dichlorophenyl)bicyclo[2,2,2]octane as white crystals (14 g.). Similarly the following compounds were prepared:

trans-3-cyano-2-phenylbicyclo[2,2,2]octane
trans-3-cyano-2-p-aminophenylbicyclo[2,2,2]octane
trans-3-cyano-2-p-methylphenylbicyclo[2,2,2]octane
trans-3-cyano-2-p-methoxyphenylbicyclo[2,2,2]octane
trans-3-cyano-2-p-N-acetylaminophenylbicyclo[2,2,2]octane
trans-3-cyano-2-p-N,N-dimethylaminophenylbicyclo[2,2,2]octane

EXAMPLE 8

Orthophosphoric acid (40 drops) was added at 0°C. to trans-2-phenylbicyclo[2,2,2]octane-3-carboxaldehyde (21.4 g.) in acetic anhydride (100 ml.). After 1 hour, nitric acid (9 ml., density 1.42) was added dropwise at 0°C. and the temperature allowed to rise to 20°C. overnight. The mixture was then stirred in water (400 ml.) and concentrated hydrochloric acid (20 ml.) for 3 hours, followed by extraction with dichloromethane. After washing with saturated sodium carbonate solution and drying over magnesium sulphate, the dichloromethane extract was evaporated to give an oil. The latter was refluxed in a solution containing ethanol (120 ml.), concentrated sulphuric acid (8.0 ml.) and water (80 ml.) for 2½ hours. A large excess of water was added followed by extraction with dichloromethane. The extract was shaken with saturated sodium carbonate solution, dried and evaporated to give an oil which on crystallisation from petroleum ether (b.p. 60° – 80°C.) yielded trans-2-p-nitrophenylbicyclo[2,2,-2]octane-3-carboxaldehyde, m.p. 92° – 93°C. Similarly nitration of trans-6-phenylbicyclo[2,2,2]oct-2-ene-5-carboxaldehyde yields trans-6-p-nitrophenylbicyclo[2,2,2]oct-2-ene-5-carboxaldehyde. The latter on reduction by the method of Example 1 gives trans-2-p-aminophenylbicyclo[2,2,2]octane-3-carboxaldehyde.

The following Examples will illustrate the preparation of compounds of formula I above:

EXAMPLE 9

The aldehyde from Example 1 (12.84 g.) was dissolved in ethanol (80 ml.). A solution prepared from 35% ethanolic methylamine (16.2 ml.) and glacial acetic acid (7.2 g.) was added and the solution was hydrogenated over 5% palladium/charcoal (0.5 g.) at 60 pounds/sq. in. Hydrogen uptake was 80% complete after 2 hours and 100% complete after 16 hours. The bulk of the ethanol was removed under reduced pressure and water (ca. 500 ml.) added. The solution was basified by addition of 2N-sodium hydroxide and extracted with three portions of methylene chloride. The combined extracts were dried over magnesium sulphate, filtered and evaporated to give N-methyl-trans-2-phenylbicyclo[2,2,2]oct-3-ylmethylamine (14 g.) as a viscous oil. The hydrochloride was prepared in conventional manner and re-crystallised from isopropanol, m.p. 233° – 235°C.

EXAMPLE 10

2-(trans-2-Phenylbicyclo[2,2,2]oct-3-yl)ethyl isocyanate (25 g.) was suspended in concentrated hydrochloric acid (200 ml.) and heated under reflux for 16 hours after which time evolution of carbon dioxide had ceased. The aqueous acid was removed by evaporation under reduced pressure and the resultant hydrochloride was dissolved in chloroform. The solution was filtered and petroleum ether was added until crystallisation began. The white crystals (17 g.) were re-crystallised from chloroform/ether to give 2-(trans-2-phenylbicyclo[2,2,2]oct-3-yl)ethylamine hydrochloride, m.p. 209° – 211°C.

The same compound was also prepared by the method of Example 9 using trans-2-phenylbicyclo[2,2,-2]oct-3-yl acetaldehyde and ammonia as reactants or by applying the reduction method described in the first paragraph of Example 11 to trans-2-phenylbicyclo[2,2,2]oct-3-yl-acetamide or -acetonitrile.

A solution of 2-(trans-2-phenylbicyclo[2,2,2]oct-3-yl)ethylamine hydrochloride (16.3 g.), formaldehyde (4.25 ml. of 37% w/v solution), formic acid (5.4 g.) and sodium formate (1.61 g.) was heated under gentle reflux overnight. Further formaldehyde (4.25 ml.) and formic acid (5.4 g.) were added and heating continued for a further 12 hours. The resultant solution was dissolved in 2N-hydrochloric acid and washed with methylene chloride. After basification with 2N-sodium hydroxide, the solution was extracted three times with methylene chloride, the combined extracts dried over magnesium sulphate and evaporated to give the free amine as an oil. By treatment with ethereal hydrogen chloride, N,N-dimethyl 2-(trans-2-phenylbicyclo[2,2,-2]oct-3-yl)ethylamine hydrochloride, m.p. 221° – 223°C., was obtained.

EXAMPLE 11

3-(trans-2-Phenylbicyclo[2,2,2]oct-3-yl)propionamide (6.425 g.) was dissolved in tetrahydrofuran (100 ml.) and the solution added slowly to lithium aluminium hydride (2 g.) in tetrahydrofuran (50 ml.). The suspension was stirred for 24 hours at room temperature and worked up by cautious addition of water. The solution was dried over magnesium sulphate, filtered and evaporated to give 3-(trans-2-phenylbicyclo[2,2,-2]oct-3-yl)-propylamine as an oil.

The latter, on being alkylated by the method described in Example 10 or Example 12, yielded N,N-dimethyl-3-(trans-2-phenylbicyclo[2,2,2]oct-3-yl)-propylamine hydrochloride, m.p. 192° – 194°C. and N-methyl-3-(trans-2-phenylbicyclo[2,2,2]oct-3-yl)propylamine hydrochloride, m.p. 164° – 165°C., respectively.

EXAMPLE 12

2-(trans-2-Phenylbicyclo[2,2,2]oct-3-yl)ethylamine (5.31 g.) was dissolved in ethanol (25 ml.) and triethylamine (5.1 g.) was added to the solution at 0°C. Ethyl chloroformate (2.38 g.) was added giving an immediate precipitate. The solution was stirred for 30 minutes whilst allowing it to warm to room temperature. Water was added, the solution acidified with hydrochloric acid and extracted three times with methylene chloride. The combined extracts were dried, filtered and evaporated to give an oil which was identified (n.m.r. and infra-red) as the urethane. The latter was dissolved in dry ether (50 ml.) and lithium aluminium hydride (1.2 g.) added. The suspension was stirred overnight at room temperature and then worked up by cautious addition of water and magnesium sulphate. The solution was filtered and evaporated to give N-methyl-2-(trans-2-phenylbicyclo[2,2,2]oct-3-yl) ethylamine as an oil, from which the hydrochloride was prepared, m.p. 211° – 212°C.

EXAMPLE 13

By reductive alkylation of N-methyl trans-2-phenylbicyclo[2,2,2]oct-3-yl-methylamine with acetone, propionaldehyde and butyraldehyde, there were obtained respectively N-methyl-N-isopropyl trans-2-phenylbicyclo[2,2,2]oct-3-ylmethylamine hydrochloride, m.p. 164° – 165°C., N-methyl-N-n.propyl trans-2-phenylbicyclo[2,2,2]oct-3-ylmethylamine hydrochloride, m.p. 151°C., and N-methyl-N-n.butyl trans-2-phenylbicyclo[2,2,2]oct-3-ylmethylamine, m.p. 130° – 132°C.

EXAMPLE 14

By the method of Example 9 but using trans-2-p-aminophenylbicyclo[2,2,2]-octane-3-carboxaldehyde and dimethylamine as reactants, there was obtained N,N-dimethyl-trans-2-p-aminophenylbicyclo[2,2,-2]oct-3-yl methylamine which was isolated as its dimaleate salt, m.p. 138° – 140°C.

Alternatively the following method, which involves reductive alkylation of the above aldehyde in situ in the reaction medium in which it is formed, may be used:

trans-6-p-Nitrophenylbicyclo[2,2,2]oct-2-ene-5-carboxaldehyde (11 g.), anhydrous dimethylamine (60 ml.) and dichloromethane (300 ml.) were hydrogenated at atmospheric pressure in the presence of 5% palladium on charcoal (1 g.). After 24 hours, the solution was filtered, shaken with dilute sodium hydroxide, dried and evaporated to give the desired dimethylamine as a white waxy solid. The latter was dissolved in ethanol (50 ml.) and, on adding maleic acid (8.8 g.) in ethanol, yielded N,N-dimethyl-trans-2-p-aminophenylbicyclo[2,2,2]oct-3-yl methylamine dimaleate, m.p. 138° – 140°C.

EXAMPLE 15

A mixture of N,N-dimethyl-trans-2-p-aminophenylbicyclo[2,2,2]oct-3-yl methylamine (3 g.), formaldehyde (2 ml. of a 40% solution in water), acetic acid (15 ml.), ethanol (60 ml.) and 5% palladium on charcoal (0.5 g.) was hydrogenated at 60 pounds/sq. in. for 2 days. The solution was filtered, diluted with 5 N hydrochloric acid and extracted with ether. The aqueous layer was basified and extracted with ether. The combined ether extracts were dried and evaporated to give a colourless oil which, on addition of ethanolic hydrochloric acid, yielded a white solid. The latter was recrystallised from ethanol/ether giving N,N-dimethyl-trans-2-p-dimethylaminophenylbicyclo[2,2,2]oct-3-yl methylamine dihydrochloride, m.p. 224° – 226°C. (sublimed).

The latter compound can also be obtained by the method described in Example 9 using trans-2-p-dimethylaminophenylbicyclo[2,2,2]octane-3-carboxaldehyde and dimethylamine as reactants.

EXAMPLE 16

By the method of Example 10 but starting with trans-2-p-N-acetylaminophenylbicyclo[2,2,2]oct-3-yl methyl isocyanate, there was obtained N,N-methyl-trans-2-p-N-acetylaminophenylbicyclo[2,2,2]oct-3-yl methylamine hydrochloride, m.p. 230° – 235°C.

The latter compound can also be obtained by acetylation of the corresponding 2-p-aminophenyl compound as follows:

To N,N-dimethyl-trans-2-p-aminophenylbicyclo[2,2,2]oct-3-yl methylamine (3 g.) in dichloromethane (50 ml.) and triethylamine (5 ml.), acetic anhydride (3 ml.) was added. After stirring overnight, dilute hydrochloric acid (10 ml.) was added and the mixture extracted with ether. Basification followed by re-extraction with ether, drying and evaporation produced on oil which, on treatment with ethanolic hydrochloric acid, gave the desired hydrochloride salt, m.p. 232° – 235°C.

EXAMPLE 17 trans-3-Cyano-2-(3',4'-dichlorophenyl)bicyclo[2,2,2]octane (4.1 g.) was added to lithium aluminium hydride (0.55 g.) in tetrahydrofuran (55 ml.). After 3 hours, water was added and the mixture extracted with ether. Evaporation of the ether extract yielded 2-(3',4'-dichlorophenyl)bicyclo[2,2,2]oct-3-yl methylamine as an oil (4 g.). The latter, ethanol (25 ml.), acetic acid (7 ml.), 10% palladium on charcoal (0.5 g.) and formaldehyde (3.7 ml. of 40% solution) were hydrogenated at atmospheric pressure for 24 hours. The catalyst was filtered off and dilute hydrochloric acid added. After extraction with ether, the aqueous layer was basified and again extracted with ether. The combined ether extracts were evaporated to give an oil which, on treatment with ethanolic hydrochloric acid, yielded N,N-dimethyl-trans-2-(3',4'-dichlorophenyl)bicyclo[2,2,2]oct-3-yl methylamine hydrochloride which gave a satisfactory C, H, N and Cl analysis.

Similarly N,N-dimethyl-trans-2-p-chlorophenylbicyclo[2,2,2]oct-3-yl methylamine hydrochloride, m.p. 244° – 245°C., and N-methyl-N-ethyl-trans-2-p-chlorophenylbicyclo[2,2,2]oct-3-yl methylamine hydrochloride, m.p. 187° – 189°C., were prepared.

EXAMPLE 18

To N,N-dimethyl-trans-2-p-aminophenylbicyclo[2,2,2]oct-3-yl methylamine (0.25 g.) dissolved in 30% hydrochloric acid (2.5 ml.), sodium nitrile (0.1 g.) in water (3 ml.) was added at 0°C. After 10 minutes, cuprous chloride (0.1 g.) in 30% hydrochloric acid (2 ml.) was added at 0°C. After heating on a steam bath for 15 minutes, the mixture was extracted with ether. The aqueous layer was basified and further extracted with ether. Evaporation of the combined, dried ether extracts gave a yellow oil which, on treatment with ethanolic hydrochloric acid, yielded N,N-dimethyl-trans-2-p-chlorophenylbicyclo[2,2,2]oct-3-yl methylamine hydrochloride, m.p. 244° – 245°C. Similarly, by using cuprous bromide instead of cuprous chloride, N,N-dimethyl-trans-2-p-bromophenylbicyclo[2,2,2]oct-3-yl methylamine hydrochloride was obtained.

Alternatively, after preparation of the diazonium salt as described above, it can be decomposed in methanol to yield N,N-dimethyl-trans-2-p-methoxyphenylbicyclo[2,2,2]oct-3-yl methylamine hydrochloride.

EXAMPLE 19

Ethyl trans-2-p-methylphenylbicyclo[2,2,2]octane-3-carboxylate (0.025 mole) was added to lithium aluminium hydride (0.03 mole) in tetrahydrofuran (60 ml.) at 0°C. and after 3 hours, water was added and the mixture extracted with ether. Evaporation of the ether extract gave the corresponding bicyclo[2,2,2]oct-3-yl methanol as an oil. The latter was dissolved in dichloromethane (50 ml.) and methylamine (10 ml.) and methanesulphonyl chloride (3.6 g.) added at 0°C. After 2 hours, dimethylamine (25 ml. of a 33% solution in water) was added to the resultant methyl sulphonate and the mixture refluxed for 1 week. A large excess of water was added and the mixture extracted with ether. Evaporation of the dried ether extract yielded a solid which, on addition of ethanolic hydrochloric acid, gave N,N-dimethyl-2-p-methylphenylbicyclo[2,2,2]oct-3-yl methylamine hydrochloride as a white solid (2 g.) which had a satisfactory C, H, N and Cl analysis. Similarly, N,N-dimethyl-2-p-methoxyphenylbicyclo[2,2,2]oct-3-yl methylamine hydrochloride was prepared. Also by reduction of trans-2-p-nitrophenylbicyclo[2,2,2]octane-3-carboxyaldehyde, using sodium borohydride, followed by treatment of the resultant methanol as described above, N,N-dimethyl-2-p-nitrophenylbicyclo[2,2,2]oct-3-yl methylamine hydrochloride was obtained.

EXAMPLE 20

Using the methods described in Examples 9 to 19, the following compounds were prepared, melting points given referring to those compounds isolated in hydrochloride salt form:

N-t.butyl trans-2-phenylbicyclo[2,2,2]oct-3-ylmethylamine

N,N-dimethyl-trans-2-phenylbicyclo[2,2,2]oct-3-ylmethylamine, m.p. 231° – 232°C.

N-ethyl-trans-2-phenylbicyclo[2,2,2]oct-3-ylmethylamine, m.p. 214° – 216°C. (dec.)

N,N-diethyl-trans-2-phenylbicyclo[2,2,2]oct-3-ylmethylamine, m.p. 164° – 165°C.

N-methyl-N-ethyl-trans-2-phenylbicyclo[2,2,2]oct-3-ylmethylamine, m.p. 178° – 180°C.

N-methyl-3-(trans-2-p-aminophenylbicyclo[2,2,2]oct-3-yl)propylamine

N,N-dimethyl-3-(trans-2-p-aminophenylbicyclo[2,2,2]oct-3-yl)propylamine

N-methyl-N-ethyl-2-(trans-2-p-chlorophenylbicyclo[2,2,2]oct-3-yl)ethylamine

N,N-dimethyl-2-(trans-2-p-ethoxyphenylbicyclo[2,2,2]oct-3-yl)ethylamine

N-methyl-2-(trans-2-p-aminophenylbicyclo[2,2,2]oct-3-yl)ethylamine

EXAMPLE 21 trans m-Chlorocinnamonitrile m-Chlorobenzaldehyde (210.75 g; 1.5 m), cyanoacetic acid (127.5 g; 1.5 m) and pyridine (150 ml.) were refluxed for two days. The solution was evaporated to give an oil which was distilled to give a mixture of isomers (72% trans/23% cis; 5% aldehyde), Yield (129 g; 53%), b.p. 70°–85°C. at 0.8 mm. The material was dissolved in isopropanol and allowed to fractionally crystallise at 0°C. The solid was filtered and freeze-dried. Yield of pure trans isomer was 15 g (6.1%) b.p. 104°–106°C. at 1 mm; m.p. 26°–28°C.

trans-6-(m-Chlorophenyl)-Bicyclo-[2,2,2]-oct-2-ene-5-carbonitrile trans-m-Chlorocinnamonitrile prepared as above (9.2 g; 0.056 m) and 1,3-cyclohexadiene (8.03 ml; 0.084 m) were added to a sealed tube with a trace of hydroquinone and 1,2-dichlorobenzene, and heated at 150°–160°C. for 2 weeks. The solution was evaporated to give a golden oil (12 g) which was washed several times with cold 40°–60°C. petrol, and then repeatedly with hot 60°–80°C. petrol. These latter washings were collected and reduced to a viscous oil (10.2 g; 75%).

trans-2-(m-Chlorophenyl)bicyclo[2,2,2]-octane-3-carbonitrile trans-6-(m-Chlorophenyl)bicyclo[2,2,2]-oct-2-ene-5-carbonitrile prepared as above (9.4 g; 0.038 m) was hydrogenated in ethanol at atmospheric pressure in the presence of 5% Palladium on charcoal (1.0 g). After the theoretical amount of hydrogen uptake, the catalyst was filtered off and the solution reduced to an oil (9.1 g; 97%). This was crystallised by dissolving in ethanol m.p. 112°–113°C.

Analysis: Calc: C 73.32; H 6.56; N 5.7; Cl 14.43. Found: C 73.43; H 6.41; N 5.82; Cl 14.38.

trans-2-(m-Chlorophenyl)bicyclo[2,2,2]oct-3-yl methylamine hydrochloride trans-2-(m-Chlorophenyl)bicyclo[2,2,2]-octane-3-carbonitrile prepared as above (8.0 g; 0.032 m) in dry tetrahydrofuran (20 ml) was added dropwise to a chilled and stirred solution of lithium aluminium hydride (1.61 g; 0.042 m) in dry tetrahydrofuran (20 ml). After the addition, the solution was allowed to warm up to room temperature and was stirred overnight. 5N Sodium hydroxide (1.6 ml) and then water (7 ml.) were added cautiously to produce a fine white precipitate which was filtered. The filtrate was dried over magnesium sulphate, and evaporated, after filtration, to an oil which produced, on dissolving in ethanolic hydrochloric acid and slowly adding ether, the hydrochloride salt (6.8 g; 74%) m.p. 220°–2°C.

N,N-Dimethyl-trans-2-(m-chlorophenyl)bicyclo[2,2,-2]oct-3-yl methylamine hydrochloride To the trans-2-(m-chlorophenyl)bicyclo[2,2,2]oct-3-yl methylamine hydrochloride prepared above (3.0 g; 0.011 m) was added sodium hydrogen carbonate (0.92 g; 0.011 m) and dimethyl formamide (30 ml.). The flask was cooled to 0°C. and a mixture of formic acid 90% (2.29 ml; 0.055 m) and formaldehyde 37–40% (3.78 ml; 0.055 m) was added slowly. After addition, the solution was slowly heated to reflux. After five hours, the solution was cooled, added to water (80 ml.), made alkaline with solid potassium hydroxide (pH=8) and extracted with ethyl acetate (3 × 30 ml.). The combined organic phase was washed with water (2 × 30 ml.), dried over magnesium sulphate, filtered and the solvent removed in vacuo to give an oil (2.10 g; 61%). Hydrochloride salt formed using ethanolic hydrochloric acid and the title compound was recrystallised from ethanol ether (2.1 g) m.p. 217°–219°C.

Analysis: Calc: C 64.96; H 8.01; N 4.45; Cl 22.56. Found: C 64.67; H 7.82; N 4.44; Cl 22.64.

I claim:

1. Compound of the formula:

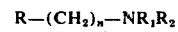

R—(CH$_2$)$_n$—NR$_1$R$_2$     I.

and acid addition salts thereof, wherein $n$ is an integer from 1 to 3, R$_1$ is C$_{1-4}$ alkyl, R$_2$ is hydrogen or C$_{1-4}$ alkyl and R is a trans 2-phenylbicyclo[2,2,2]oct-3-yl group of formula:

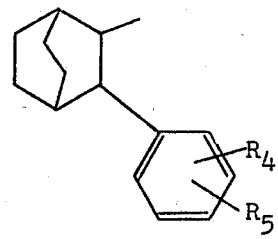

(II)

wherein R$_4$ and R$_5$ represent the same or different substituent selected from hydrogen, halogen, nitro, amino, mono- or di-C$_{1-4}$ alkylamino, C$_{1-4}$ alkyl or C$_{1-4}$ alkoxy.

2. Compound according to claim 1, wherein $n$ is 1 or 2, R$_4$ and R$_5$ are hydrogen, R$_1$ is C$_{1-4}$ alkyl and R$_2$ is hydrogen, methyl or ethyl.

3. Compound according to claim 1, wherein $n$ is 1 or 2, R$_1$ is C$_{1-4}$ alkyl, R$_2$ is hydrogen, methyl or ethyl, R$_5$ is hydrogen and R$_4$ is halogen, nitro, amino, methyl- or ethylamino, dimethyl- or diethylamino, methyl, ethyl, methoxy or ethoxy in the 4-position.

4. Compound according to claim 2, said compound being N,N-dimethyl-trans-2-phenylbicyclo[2,2,2]oct-3-yl methylamine or an acid addition salt thereof.

5. Compound according to claim 2, said compound being N-methyl-2-(trans-2-phenylbicyclo[2,2,2]oct-3-yl) ethylamine or an acid addition salt thereof.

6. Compound according to claim 2, said compound being N-ethyl-trans-2-phenylbicyclo[2,2,2]oct-3-yl methylamine or an acid addition salt thereof.

7. Compound according to claim 2, said compound being N-methyl-N-ethyl-trans-2-phenylbicyclo[2,2,2]oct-3-yl methylamine or an acid addition salt thereof.

8. Compound according to claim 2, said compound being N,N-diethyl-trans-2-phenylbicyclo[2,2,2]oct-3-yl methylamine or an acid addition salt thereof.

9. Compound according to claim 3, said compound being N,N-dimethyl-trans-2-p-chlorophenylbicyclo[2,2,2]oct-3-yl methylamine or an acid addition salt thereof.

10. Compound according to claim 3, said compound being N,N-dimethyl-trans-2-p-aminophenylbicyclo[2,2,2]oct-3-yl methylamine or an acid addition salt thereof.

11. Compound according to claim 1, wherein $n$ is 1, $R_1$ and $R_2$ are methyl, $R_5$ is hydrogen and $R_4$ is a meta-halogen substituent, or an acid-addition salt thereof.

12. Compound according to claim 1, said compound being N,N-dimethyl-trans-2-(m-chlorophenyl)bicyclo[2,2,2]oct-3-yl methylamine or an acid addition salt thereof.

13. N,N-dimethyl-trans-2-(m-chlorophenyl)bicyclo[2,2,2]oct-3-yl methylamine hydrochloride.

14. Pharmaceutical composition in dosage unit form comprising as active ingredient a chemotherapeutically effective amount of a compound of the formula:

$$R-(CH_2)_n-NR_1R_2 \qquad I.$$

or a pharmaceutically acceptable acid-addition salt thereof, wherein $n$ is an integer from 1 to 3, $R_1$ is $C_{1-4}$ alkyl, $R_2$ is hydrogen or $C_{1-4}$ alkyl and R is a trans 2-phenybicyclo[2,2,2] oct-3-yl group of formula:

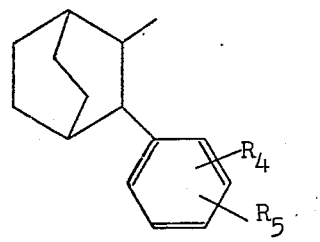

II wherein $R_4$ and $R_5$ represent the same or a different substituent selected from hydrogen, halogen, nitro, amino, mono- or di-$C_{1-4}$ alkylamino, $C_{1-4}$ alkyl or $C_{1-4}$ alkoxy, associated with a pharmaceutically acceptable carrier therefor.

15. Composition according to claim 14, wherein the compound of formula I is a compound in which $n$ is 1, $R_1$ and $R_2$ are both methyl, $k_5$ is hydrogen and $R_4$ is a meta halo substituent.

16. Composition according to claim 15 wherein $R^4$ is a meta-chloro substituent.

* * * * *